United States Patent [19]

Gaughan

[11] 4,119,432
[45] Oct. 10, 1978

[54] HERBICIDAL N-(DIALKYLCARBAMYL)-N-TRIFLUOROMETHYL-PHENYLCARBAMYL ALKYL DISULFIDES

[75] Inventor: Edmund J. Gaughan, Berkeley, Calif.

[73] Assignee: Stauffer Chemical Company, Westport, Conn.

[21] Appl. No.: 797,717

[22] Filed: May 17, 1977

[51] Int. Cl.$^2$ .............. A01N 9/12; C07C 179/22
[52] U.S. Cl. .................. 71/98; 260/453 RZ
[58] Field of Search ............ 71/98, 100; 260/453 RZ, 260/455 A

[56] References Cited

U.S. PATENT DOCUMENTS

| | | | |
|---|---|---|---|
| 2,941,879 | 6/1960 | Goodhue | 71/101 |
| 3,113,857 | 12/1963 | Sheers | 260/455 A |
| 3,175,897 | 3/1965 | Tilles et al. | 71/100 |
| 3,230,243 | 1/1966 | D'Amico | 260/455 A |
| 3,385,690 | 5/1968 | Luckenbaugh | 71/120 |
| 3,428,665 | 2/1969 | Aichenegg | 71/98 |
| 3,439,018 | 4/1969 | Brookes et al. | 71/120 |

FOREIGN PATENT DOCUMENTS 2,518,544  11/1975  Fed. Rep. of Germany ...... 260/455 A

*Primary Examiner*—Glennon H. Hollrah
*Attorney, Agent, or Firm*—Joel G. Ackerman; Edith A. Rice

[57] ABSTRACT

Novel herbicidal compounds have the general formula

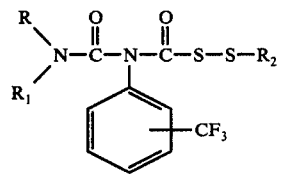

wherein each of R, $R_1$ and $R_2$ is a lower alkyl radical.

6 Claims, No Drawings

HERBICIDAL N-(DIALKYLCARBAMYL)-N-TRIFLUOROMETHYL-PHENYLCARBAMYL ALKYL DISULFIDES

This invention relates to novel carbamyl alkyl disulfides and to controlling undesired vegetation utilizing said sulfides.

The novel compounds of this invention have the formula

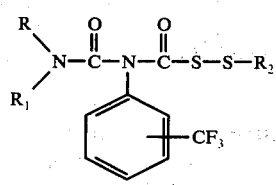

wherein each of R, $R_1$, and $R_2$ is a lower alkyl radical.

The compounds can be prepared by reacting 1-(trifluoromethylphenyl)-3,3-dialkylurea with the appropriate halocarbonyl alkyl disulfide. This reaction is represented by the following equation:

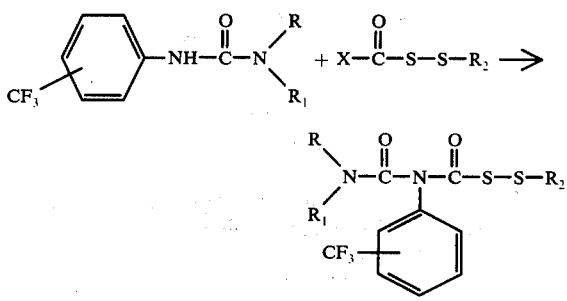

where X is halogen.

The term "lower alkyl" includes alkyl radicals containing 1-4 carbon atoms, i.e., methyl, ethyl, propyl, isopropyl, butyl, isobutyl, sec-butyl, and tert-butyl.

Illustrative examples of compounds encompassed by the instant invention are:

N-(dimethylcarbamyl)-N-m-trifluoromethylphenyl carbamyl ethyl disulfide,
N-(methylethylcarbamyl)-N-m-trifluoromethylphenyl carbamyl methyl disulfide,
N-(methylpropylcarbamyl)-N-m-trifluoromethylphenyl carbamyl propyl disulfide,
and
N-(dibutylcarbamyl)-N-m-trifluoromethylphenyl ethyl disulfide.

EXAMPLE

The following example illustrates in detail the preparation of N-(dimethylcarbamyl)-N-trifluoromethylphenyl carbamyl ethyl disulfide.

To sodium hydride (9.1 grams, 0.38 mole) in 150 milliliters dry tetrahydrofuran was added a solution of 1-(m-trifluoromethylphenyl)-3,3-dimethylurea (81 grams, 0.35 mole) in 650 milliliters tetrahydrofuran at room temperature. The mixture was stirred 1 hour at room temperature and one hour at 40°-45° C. The resulting solution was added rapidly dropwise to chlorocarbonyl ethyl disulfide (59.5 grams, 0.38 mole) in 200 milliliters tetrahydrofuran. The temperature was allowed to rise to 33° C. The mixture stood overnight at room temperature and was then warmed to 40°-45° C. for 1 hour. After the solvent had been removed in vacuo, the residue was taken up in 300 milliliters benzene and 250 milliliters of 5% sodium bicarbonate solution and filtered through Celite. The organic phase was washed with bicarbonate solution, dried, and evaporated. Upon standing, the crude material deposited a solid which was separated and crystallized twice from benzenehexane. m.p. 76°-78°; yield 25.8 grams (21% of theory). The structure was confirmed by IR, NMR, and MS.

The herbicidal activity of this compound is shown by the following herbicidal screening tests.

PRE-EMERGENCE HERBICIDE SCREENING TEST

Using an analytical balance, 20 mg of the compound to be tested is weighted out on a piece of glassine weighing paper. The paper and compound are placed in a 30 ml wide-mouth bottle and 3 ml of acetone containing 1% Tween 20 ®(a polyoxyethylene sorbitan monolaurate) is added to dissolve the compound. If the material is not soluble in acetone, another solvent such as water, alcohol or dimethylformamide (DMF) is used instead. When DMF is used, only 0.5 ml or less is used to dissolve the compound and then another solvent is used to make the volume up to 3 ml. The 3 ml of solution is sprayed uniformly on the soil contained in a small Styrofoam flat one day after planting weed seeds in the flat of soil. A No. 152 DeVilbiss atomizer is used to apply the spray using compressed air at a pressure of 5 lb/sq. in. The rate of application is 8 lb/acre and the spray volume is 143 gal/acre.

On the day preceding treatment, the Stryofoam flat, which is 7 inches long, 5 inches wide and 2.75 inches deep, is filled to a depth of 2 inches with loamy sand soil. Seeds of seven different weed species are planted in individual rows using one species per row across the width of the flat. The seeds are covered with soil so that they are planted to a depth of 0.5 inch. The seeds used are hairy grass (*Digitaria sanguinalis*), yellow foxtail (*Setaria glauca*), redroot pigweed (*Amaranthus retroflexus*), Indian mustard (*Brassica juncea*), curly dock (*Rumex crispus*), water grass (*Echinochloa crusgalli*), and red oat (*Avena sativa*). Ample seeds are planted to give about 20 to 50 seedlings per row after emergence depending on the size of the plant.

After treatment, the flats are placed in the greenhouse at a temperature of 70° to 85° F. and watered by sprinkling. Two weeks after treatment the degree of injury or control is determined by comparison with untreated check plants of the same age. The injury rating from 0 to 100% is recorded for each species as percent control with 0% representing no injury and 100% representing complete kill. The results of this test using the compound N-(dimethylcarbamyl)-N-(trifluoromethylphenyl carbamyl ethyl disulfide are:

| | Crab-grass | Fox-tail | Wa-ter-grass | Red Oat | Pig Weed | Mus-tard | Cur-ly dock | Ave. % Con-trol |
|---|---|---|---|---|---|---|---|---|
| % Control | 100 | 100 | 100 | 100 | 100 | 100 | 100 | 100 |

POST-EMERGENCE HERBICIDE SCREENING TEST

Seeds of six plant species, including hairy crabgrass, water-grass, red oat, mustard, curly dock and Pinto beans (*Phaseolus vulgaris*) are planted in the Styrofoam flats as described above for pre-emergence screening. The flats are placed in the greenhouse at 70° to 85° F. and watered daily with a sprinkler. About 10 to 14 days after planting when the primary leaves of the bean plants are almost fully expanded and the first trifoliate leaves are starting to form, the plants are sprayed. The spray is prepared by weighing out 20 mg of the test compound, dissolving it in 5 ml of acetone containing 1% Tween 20 ® and then adding 5 ml of water. The solution is sprayed on the foliage using a No. 152 DeVilbiss atomizer at an air pressure of 5 lb/sq. in. The spray concentration is 0.2 and the rate is 8 lb/acre. The spray volume is 476 gal/acre. Injury ratings are recorded 14 days after treatment. The rating system is the same as described above in the pre-emergence test. The results of this test using the compound N-(dimethylcarbamyl)-N-(trifluormethylphenyl carbamyl ethyl disulfide are:

|  | Crab-grass | Water grass | Red oat | Mus-tard | Curly dock | Pinto Bean | Avg % Control |
|---|---|---|---|---|---|---|---|
| % Control | 100 | 100 | 100 | 100 | 100 | 100 | 100 |

The herbicidal compounds of this invention are generally applied to soil to control the growth of undesirable vegetation in the form of formulations containing the herbicidal compound and an inert carrier. Herbicidal formulations generally take the form of dusts, wettable powders, granules, solutions, or emulsifiable concentrates.

Dusts are free-flowing powder compositions containing the herbicidal composition impregnated on a particular carrier. The particle size of the carrier is usually in the range of from about 30 to 50 microns. Examples of suitable carriers are talc, bentoinite, diatomaceous earth, and pryophyllite. Anticaking and antistatic agents can be added, if desired. The composition generally contains up to 50% of active ingredient.

Wettable powders are finely divided compositions comprising a particulate carrier impregnated with the herbicidal composition and additionally containing one or more surface active agents. The surface active agent promotes, rapid dispersion of the powder in aqueous medium to form stable, sprayable suspensions. A wide variety of surface active agents can be used, for example, long chain fatty alcohols and alkali metal salts of the sulfated fatty alcohols, salts of sulfonic acid and esters of long chain fatty acids. A list of surface active agents suitable for use in agriculture formulations can be found in *Pesticide Formulations* by Wade Van Valkenburg, Marcel Dekker, Inc., N.Y. 1973 at pages 79–84.

Granules comprise the herbicidal compounds impregnated on a particulate inert carrier having a particle size of about 1 to 2 millimeters in diameter. The granules can be made by spraying a solution of the active ingredient in a volatile solvent onto the granular carrier. Suitable carriers in preparation of granules include clay, vermiculite, sawdust, granular carbon, and the like.

The herbicidal compounds can also be applied to the soil in the form of a solution in a suitable solvent. Solvents frequently used in herbicidal formulations include kerosene, fuel oil, xylene, petroleum fractions with boiling ranges above xylene, and aromatic petroleum fractions rich in methylated naphthalenes.

Emulsifiable concentrates consist of an oil solution of the herbicide along with an emulsifying agent. Prior to use the concentrate is diluted with water to form a suspended emulsion of oil droplets. The emulsifiers used are usually a mixture of anionic and nonionic surfactants. Other additives such as spreading agents and stickers can be included in the emulsifiable concentrate if desired.

The compounds are applied to the soil to control the growth of undesirable vegetation at a rate to provide about 1 to about 50, preferably about 1 to about 10, pounds per acre of active herbicidal ingredient. The amount of active ingredient used per acre will depend on overall cost and desired result.

What is claimed is:

1. A compound having the general structural formula

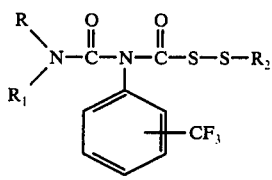

wherein each of R, $R_1$, and $R_2$ is a lower alkyl radical.

2. The compound of claim 1 wherein R and $R_1$ are each methyl and $R_2$ is ethyl.

3. A method of controlling the growth of undesired vegetation which comprises applying to the locus where control is desired a herbicidally effective amount of a compound of the formula

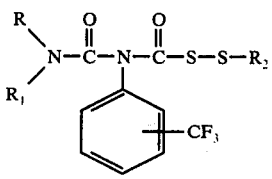

wherein each of R, $R_1$, and $R_2$ is a lower alkyl radical.

4. The method of claim 3 wherein R and $R_1$ are each methyl and $R_2$ is ethyl.

5. A herbicidal composition comprising a herbicidally effective amount of a compound of the formula

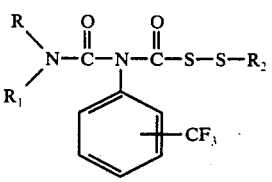

wherein each of R, $R_1$, and $R_2$ is a lower alkyl radical; and an inert carrier.

6. The composition of claim 5 wherein R and $R_1$ are each methyl and $R_2$ is ethyl.

* * * * *